United States Patent [19]

McGee

[11] Patent Number: 5,281,240
[45] Date of Patent: Jan. 25, 1994

[54] METHOD OF COLORING HAIR WITH WATER SOLUBLE ACID DYES

[75] Inventor: James B. McGee, Sanford, Mich.

[73] Assignee: Dow Corning Corporation, Midland, Mich.

[21] Appl. No.: 947,632

[22] Filed: Sep. 21, 1992

[51] Int. Cl.$^5$ .............................................. A61K 7/13
[52] U.S. Cl. ........................................... 8/405; 8/406; 8/429; 8/435; 252/174.15; 132/208; 424/70
[58] Field of Search .................. 8/405, 406, 429, 435; 252/174.15; 424/70; 132/208

[56] References Cited

U.S. PATENT DOCUMENTS

| | | | |
|---|---|---|---|
| 3,630,654 | 12/1971 | Rosenthal et al. | 8/405 |
| 4,567,039 | 1/1986 | Stadnick et al. | 8/405 |
| 4,915,938 | 4/1990 | Zawadzki | 424/70 |
| 4,950,468 | 8/1990 | Nakamura et al. | 424/70 |
| 4,960,588 | 10/1990 | Hoshowski et al. | 424/70 |
| 4,971,786 | 11/1990 | Grollier et al. | 424/70 |
| 4,973,475 | 11/1990 | Schnetzinger et al. | 424/70 |
| 4,976,952 | 12/1990 | Lang et al. | 424/70 |
| 5,008,104 | 4/1991 | Chaudhuri et al. | 424/70 |
| 5,071,441 | 12/1991 | Schnetzinger et al. | 8/405 |

FOREIGN PATENT DOCUMENTS

| | | |
|---|---|---|
| 2138845 | 10/1984 | United Kingdom . |
| 2168082 | 6/1986 | United Kingdom . |
| 2173515 | 10/1986 | United Kingdom . |

*Primary Examiner*—Paul Lieberman
*Assistant Examiner*—William S. Parks
*Attorney, Agent, or Firm*—James L. DeCesare

[57] ABSTRACT

A method of coloring hair in which there is applied to the hair a hair coloring preparation consisting essentially of a water based organic solvent free mixture of 0.01 to 10.0 percent by weight of a temporary dye color which is a water soluble acid dye, 0.1 to 10.0 percent by weight of a quaternary ammonium functional silane, the remainder of the mixture being water. The mixture is combed through the hair and the hair is allowed to dry without rinsing.

8 Claims, No Drawings

METHOD OF COLORING HAIR WITH WATER SOLUBLE ACID DYES

BACKGROUND OF THE INVENTION

This invention is directed to a hair coloring method in which a temporary dye color is applied to the hair in combination with a quaternary ammonium functional silane. The inclusion of the quaternary ammonium functional silane with the temporary dye color has been found to eliminate the tendency of the temporary dye color to rub off in the presence of moisture, while allowing its removal by shampooing.

Hair colorants are divided into three basic categories. These catagories are permanent, semi-permanent, and temporary. The categories are characterized by the durability of the color imparted to the hair and the type of dye employed.

Temporary hair colorants provide a color that is removable in a single shampooing. The color attained with a temporary hair colorant represents only a temporary change of the natural hair color. Typically, they are employed in order to impart a nuance or enliven the natural hair color, to shade or renew a permanent or semi-permanent color, or to remove the yellow tinge of graying hair. High molecular weight dyes are used which deposit on the surface of the hair fiber rather than penetrating into the hair cortex. Water soluble acid dyes are representative of the class of temporary hair colorants.

While temporary hair colorants provide convenience and color flexibility for the consumer and may be easily removed from the hair by shampooing, they suffer from the disadvantage that often they may be easily removed by contact with moisture in the form of high humidity conditions, precipitation, and perspiration. This results in an undesirable tendency of the temporary hair colorant to stain the skin, clothing, and bed linens.

These disadvantages of temporary dye colorants have been overcome with the present invention in which such anionic acidic chromophores are applied to the hair in combination with certain quaternary ammonium functional silanes. The benefits derived are that the undesirable staining tendency of the temporary dye colorant is eliminated, while at the same time its desirable capability of removal by shampooing is maintained.

SUMMARY OF THE INVENTION

The invention is directed to a method of coloring hair with a temporary hair colorant in the form of a water soluble acid dye. A composition including the water soluble acid dye is applied to the hair in combination with a quaternary ammonium functional silane. While the dye can be removed by shampooing, it is stabilized against removal by casual contact with moisture. Staining is therefore eliminated. These features can be achieved by employing a preparation consisting essentially of a water based organic solvent free mixture of a water soluble acid dye and the silane, with the exclusion of organic solvents such as alcohols, ethers, and glycols.

These and other features, objects, and advantages, of the herein defined present invention will become more apparent from a consideration of the following detailed description thereof.

DETAILED DESCRIPTION OF THE INVENTION

The organosilicon quaternary ammonium functional silane in accordance with the present invention is a compound having a formula selected from the group consisting of:

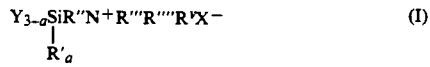 (I)

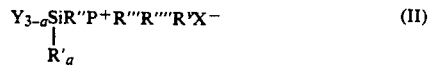 (II)

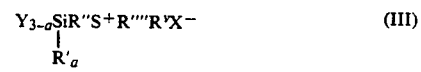 (III)

and

 (IV)

wherein in each formula (I)–(IV):

Y is R or RO where R is an alkyl radical of one to four carbon atoms or hydrogen;

$a$ has a value of zero, one or two;

R' is a methyl or ethyl radical;

R'' is an alkylene group of one to four carbon atoms;

R''', R'''' and R$^v$ are each independently selected from the group consisting of alkyl radicals of one to eighteen carbon atoms, $-CH_2C_6H_5$, $-CH_2CH_2OH$, $-CH_2OH$, and $-(CH_2)_xNHC(O)R^{vi}$ wherein x has a value of from two to ten and R$^{vi}$ is a perfluoroalkyl radical having from one to twelve carbon atoms;

X is chloride, bromide, fluoride, iodide, acetate or tosylate; and

Z is a positively charged aromatic pyridinium ring of the formula $C_5H_6N^+-$.

R in the above formulas are alkyl groups of one to four carbon atoms. Thus, useful as R in this invention are methyl, ethyl, propyl, and butyl radicals. Y can also be RO in which R is an alkyl group as noted or hydrogen indicating the silanol form, i.e. the hydrolyzate. The value of a is zero, one or two, and R' is a methyl or ethyl radical. Because of the presence of these alkyl radicals, these materials must be stabilized with a solvent. Thus, methoxy groups require methanol and ethoxy groups require ethanol.

R'' for purposes of the present invention is an alkylene group of one to four carbon atoms. Thus, R'' can be alkylene groups such as methylene, ethylene, propylene, and butylene. R''', R'''' and R$^v$ are each independently an alkyl radical of one to eighteen carbon atoms, $-CH_2C_6H_5$, $-CH_2CH_2OH$, $-CH_2OH$, or $-(CH_2)_xNHC(O)R^{vi}$. x has a value of from two to ten and R$^{vi}$ is a perfluoroalkyl radical having from one to twelve carbon atoms. X is chloride, bromide, fluoride, iodide, acetate or tosylate. Z is a positively charged aromatic pyridinium ring of the formula $C_5H_6N^+-$.

Preferred for this invention are the quaternary ammonium functional silanes of the formula

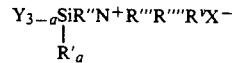

in which R is methyl or ethyl; a has a value of zero; R″ is propylene; R‴ is methyl or ethyl; R⁗ and Rᵛ are alkyl groups containing one to eighteen carbon atoms wherein at least one such group is larger than eight carbon atoms; and X is either chloride, acetate or tosylate.

Specific quaternary ammonium functional silanes within the scope of the present invention are represented by compounds having the following formulas:

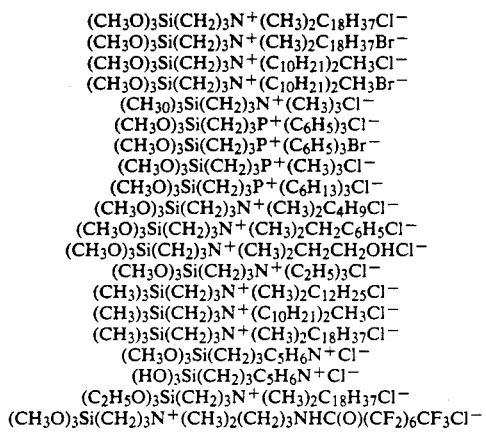

One particularly preferred species of quaternary ammonium functional silane compound corresponding to formula (I) is 3-(trimethoxysilyl)propyldimethyloctadecyl ammonium chloride of the structure:

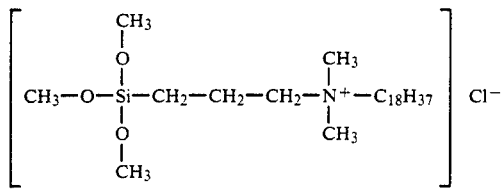

This compound will be referred to hereinafter as "TMS" for the sake of simplicity.

Quaternary ammonium functional silanes are compounds which include in the molecular structure a central nitrogen atom joined to four organic groups and a negatively charged acid radical such as halogen. The use of a quaternary ammonium functional silane compound is based on the hydrophilic portion of the molecule which bears a positive charge. Since most surfaces are negatively charged, these cationic surface active agents are readily adsorbed to negatively charged surfaces. This affinity for negatively charged surfaces is exhibited by the species 3-(trimethoxysilyl)propyldimethyloctadecyl ammonium chloride.

In the presence of moisture, this silane imparts a durable, wash resistant, broad spectrum biostatic surface antimicrobial finish to a substrate. This quaternary ammonium functional silane compound is leach resistant, nonmigrating, and is not consumed by microorganisms. It is effective against gram positive and gram negative bacteria, fungi algae, yeasts, mold, rot, and mildew. This silane is capable of providing durable, bacteriostatic, fungistatic, and algistatic surfaces.

After the silane is applied to a surface, it is chemically bonded to the substrate by condensation of the silanol groups at the surface. What is important is the fact that the durability of any effect produced by the silane as part of a product requires that the silane molecule react with a surface to a certain extent. The most reactive species, as far as the silanes are concerned, is ≡SiOH that is formed by hydrolysis of the alkoxy groups present on the silane. The ≡SiOH groups react with the surface and bind the silane to the surface. It is believed that even though the prime mode of coupling to a surface system is by the route described above, that the alkoxy groups on the silicon atom participate in their own right to bind the silane to a surface.

Methods of making quaternary ammonium functional silanes are known in the art and involve the reaction of chloroalkyltrimethoxysilanes and tertiary amines. For example, the specific silane "TMS" can be prepared as follows:

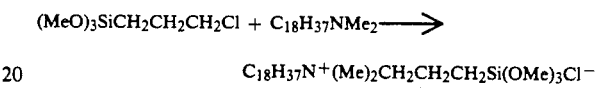

$$C_{18}H_{37}N^+(Me)_2CH_2CH_2CH_2Si(OMe)_3Cl^-$$

Such bound-type silanes function differently from traditional organic unbound agents in that the bound silane actually attaches itself to the surface to which it is applied, whereas the unbound organic is typically a coating which is not substantive.

The temporary dye color used in accordance with the present invention is a water soluble acid dye. Representative water soluble acid dyes which can be employed are compounds having The Colour Index name and formula selected from the group consisting of Acid Blue 9 of the formula $C_{37}H_{36}N_2O_9S_3.2Na$; Acid Green 3 of the formula $C_{37}H_{36}N_2O_{10}S_3.2Na$; Acid Green 25 of the formula $C_{28}H_{22}N_2O_8S_2.2Na$; Acid Orange 24 of the formula $C_{20}H_{18}N_4O_5S.Na$; Acid Red 33 of the formula $C_{16}H_{13}N_3O_7S_2.2Na$; Acid Red 87 of the formula $C_{20}H_8Br_4O_5.2Na$; Acid Violet 43 of the formula $C_{21}H_{15}NO_6S.Na$; and Acid Yellow 1 of the formula $C_{10}H_6N_2O_8S.2Na$.

The method of coloring hair in accordance with the present invention comprises applying to the hair a hair coloring preparation consisting essentially of a water based organic solvent free mixture of 0.01 to 10.0 percent by weight of a temporary dye color, which as noted above, is a water soluble acid dye, 0.1 to 10.0 percent by weight of the quaternary ammonium functional silane, with the remainder of the mixture being water. Preferably, the mixture contains one to five percent by weight of the silane. The mixture is combed through the hair, and the hair is allowed to dry without rinsing.

The temporary dye color may be displaced from the hair by contacting the hair with a shampoo composition which includes an anionic surfactant in order to restore the original hair color, and the hair can be re-colored again by repeating the method defined above. The anionic surfactant such as sodium lauryl sulfate displaces the chromophore in restoring the hue.

The present invention is set forth in more detail in the following examples.

EXAMPLE I

A commercial brand rouge fizz-in color mousse was squirted into an eight ounce french square bottle. The foam was allowed to collapse. Ten grams of the fluid were diluted to one hundred grams with deionized water to provide a 1:10 color solution. Serial dilutions of the quaternary ammonium functional silane "TMS"

were prepared at concentrations of 1:10, 1:100, and 1:1000, in deionized water. The color solution and the "TMS" serial dilutions were combined into Sample Nos. 1-4 as shown below in Table I.

TABLE I

| Grams | 1 | 2 | 3 | 4 |
|---|---|---|---|---|
| 1:10 Color Solution | 9 | 9 | 9 | 9 |
| 1:10 "TMS" Dilution | — | 1 | — | — |
| 1:100 "TMS" Dilution | — | — | 1 | — |
| 1:1000 "TMS" Dilution | — | — | — | 1 |
| Deionized Water | 1 | — | — | — |
| Clarity | Hazy | Clear | Hazy | Hazy |
| Color | Red | Orange | Red/Orange | Red |
| Towel Stain | Bad | None | Bad | Bad |

EXAMPLE II

The towel stain test shown above in Table I was performed by treating one gram hair tresses with each of the Sample Nos. 1-4. Each tress was blow dried, wrapped in a paper towel, soaked with deionized water, and left overnight. When the paper towel was removed from each tress, any stain which was present was noted visually and recorded.

Table I reveals that Sample No. 2 containing the 1:10 "TMS" Dilution performed the best of the four samples. Sample No. 1 was used as the control.

EXAMPLE III

Each of the dyed tresses in Example II were placed into a one-half ounce vial containing a dilute commercial brand shampoo. The shampoo included an anionic surfactant which was the compound sodium lauryl sulfate. The dyes rapidly diffused into the shampoo. After fifteen minutes, the tresses were rinsed for thirty seconds under warm tap water. All traces of the dye were removed from each tress, indicating that the practice of the concept of the present invention had eliminated dye rub-off while maintaining the capability of the dye to be removed by shampooing.

EXAMPLE IV

Examples I-III were repeated for the purpose of confirming the results, and for the purpose of optimizing the level of "TMS" required in order to eliminate stain. Six samples were prepared and tested in accordance with the procedure of Examples I-III, and the sample content and test results are shown below in Table II. The towel stain test in this example was modified from the towel stain test set forth in Example II to the extent that the towel wrapped tresses were soaked for one hour rather than overnight as in Example II.

TABLE II

| Grams | 1 | 2 | 3 | 4 | 5 | 6 |
|---|---|---|---|---|---|---|
| 1:10 Color Solution | 9 | 9 | 9 | 9 | 9 | 9 |
| 1:10 "TMS" Dilution | — | 0.2 | 0.4 | 0.6 | 0.8 | 1 |
| Deionized Water | 1 | 0.8 | 0.6 | 0.4 | 0.2 | — |
| Clarity | Hazy | Hazier | Hazier | Slight | Clear | Clear |
| Color | Red | Red/Orange | Orange | Orange | Orange | Orange |
| Towel Stain | Bad | Slight | None | None | None | None |

The results in Table II indicate that the most effective hair coloring preparations contain about 0.4 to one percent by weight of the quaternary ammonium functional silane, most preferably about one percent by weight of the quaternary ammonium functional silane.

EXAMPLE VI

Examples I-III were repeated using other commercial brand color styling mousses with the same results.

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. A method of coloring hair comprising applying to the hair a hair coloring preparation consisting essentially of an organic solvent free mixture of 0.01 to 10.0 percent by weight of a temporary dye color which is a water soluble acid dye, 0.1 to 10.0 percent by weight of a cationic silane, the remainder of the mixture being water; combing the mixture through the hair; and allowing the hair to dry without rinsing.

2. A method according to claim 1 in which the temporary dye color is displaced from the hair by contacting the hair with a shampoo composition which includes an anionic surfactant, and the hair is re-colored by repeating the method defined in claim 1.

3. A method according to claim 1 in which the temporary dye color is a compound having The Colour Index name and formula selected from the group consisting of Acid Blue 9 of the formula $C_{37}H_{36}N_2O_9S_3\cdot 2Na$; Acid Green 3 of the formula $C_{37}H_{36}N_2O_{10}S_3\cdot 2Na$; Acid Green 25 of the formula $C_{28}H_{22}N_2O_8S_2\cdot 2Na$; Acid Orange 24 of the formula $C_{20}H_{18}N_4O_5S\cdot Na$; Acid Red 33 of the formula $C_{16}H_{13}N_3O_7S_2\cdot 2Na$; Acid Red 87 of the formula $C_{20}H_8Br_4O_5\cdot 2Na$; Acid Violet 43 of the formula $C_{21}H_{15}NO_6S\cdot Na$; and Acid Yellow 1 of the formula $C_{10}H_6N_2O_8S\cdot 2Na$.

4. A method according to claim 1 in which the silane is a compound having a formula selected from the group consisting of:

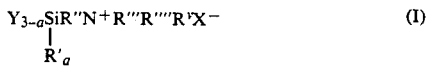     (I)

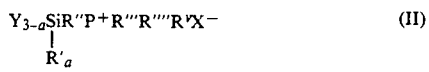     (II)

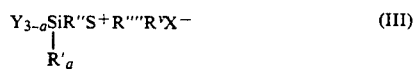     (III)

and

     (IV)

wherein in each formula (I)-(IV):
Y is R or RO where R is an alkyl radical of one to four carbon atoms or hydrogen;

a has a value of zero, one or two;

R' is a methyl or ethyl radical;

R'' is an alkylene group of one to four carbon atoms;

R''', R'''' and R$^v$ are each independently selected from the group consisting of alkyl radicals of one to eighteen carbon atoms, —CH$_2$C$_6$H$_5$, —CH$_2$C-H$_2$OH, —CH$_2$OH, and —(CH$_2$)$_x$NHC(O)R$^{vi}$ wherein x has a value of from two to ten and R$^{vi}$ is a perfluoroalkyl radical having from one to twelve carbon atoms;

X is chloride, bromide, fluoride, iodide, acetate or tosylate; and

Z is a positively charged aromatic pyridinium ring of the formula C$_5$H$_6$N$^+$—.

5. A method according to claim 4 in which the mixture includes 1 to 5.0 percent by weight of the silane.

6. A method according to claim 4 in which the silane has the formula (I):

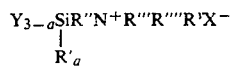

in which R is methyl or ethyl; a has a value of zero; R'' is propylene; R''' is methyl or ethyl; R'''' and R$^v$ are alkyl groups containing one to eighteen carbon atoms wherein at least one such group is larger than eight carbon atoms; and X is chloride, acetate or tosylate.

7. A method according to claim 6 in which the silane is the compound 3-(trimethoxysilyl)propyldimethyloctadecyl ammonium chloride of the formula:

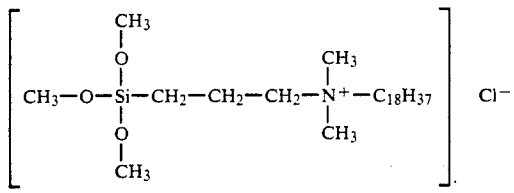

8. A method of coloring hair comprising applying to the hair a hair coloring preparation consisting essentially of an organic solvent free mixture of 0.01 to 10.0 percent by weight of a temporary dye color which is a water soluble acid dye, 0.1 to 10.0 percent by weight of a cationic silane, the remainder of the mixture being water; combing the mixture through the hair; and allowing the hair to dry without rinsing; the temporary dye color being a compound having The Colour Index name and formula selected from the group consisting of Acid Blue 9 of the formula C$_{37}$H$_{36}$N$_2$O$_9$S$_3$.2Na; Acid Green 3 of the formula C$_{37}$H$_{36}$N$_2$O$_{10}$S$_3$.2Na; Acid Green 25 of the formula C$_{28}$H$_{22}$N$_2$O$_8$S$_2$.2Na; Acid Orange 24 of the formula C$_{20}$H$_{18}$N$_4$O$_5$S.Na; Acid Red 33 of the formula C$_{16}$H$_{13}$N$_3$O$_7$S$_2$.2Na; Acid Red 87 of the formula C$_{20}$H$_8$Br$_4$O$_5$.2Na; Acid Violet 43 of the formula C$_{21}$H$_{15}$NO$_6$S.Na; and Acid Yellow 1 of the formula C$_{10}$H$_6$N$_2$O$_8$S.2Na.; the silane being a compound having a formula selected from the group consisting of:

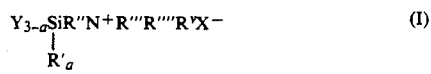 (I)

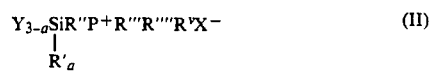 (II)

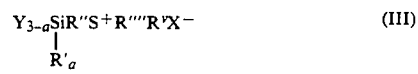 (III)

and

 (IV)

wherein in each formula (I)–(IV):

Y is R or RO where R is an alkyl radical of one to four carbon atoms or hydrogen;

a has a value of zero, one or two;

R' is a methyl or ethyl radical;

R'' is an alkylene group of one to four carbon atoms;

R''', R'''' and R$^v$ are each independently selected from the group consisting of alkyl radicals of one to eighteen carbon atoms, —CH$_2$C$_6$H$_5$, —CH$_2$C-H$_2$OH, —CH$_2$OH, and —(CH$_2$)$_x$NHC(O)R$^{vi}$ wherein x has a value of from two to ten and R$^{vi}$ is a perfluoroalkyl radical having from one to twelve carbon atoms;

X is chloride, bromide, fluoride, iodide, acetate or tosylate; and

Z is a positively charged aromatic pyridinium ring of the formula C$_5$H$_6$N$^+$—.

* * * * *